United States Patent [19]

Sutherland

[11] Patent Number: 4,873,967
[45] Date of Patent: Oct. 17, 1989

[54] KNEE ORTHOSIS

[76] Inventor: Jeffrey L. Sutherland, 39 Ximeno Ave., Long Beach, Calif. 90803

[21] Appl. No.: 42,807

[22] Filed: Apr. 27, 1987

[51] Int. Cl.$^4$ .................................................. A61F 5/00
[52] U.S. Cl. ................................. 128/80 C; 128/80 F; 128/88; 623/39
[58] Field of Search .................... 128/86 C, 80 F, 88; 623/39, 28; 2/22

[56] References Cited

U.S. PATENT DOCUMENTS

| | | | |
|---|---|---|---|
| Re. 30,501 | 2/1981 | Almeida | 128/80 C |
| 2,144,641 | 1/1939 | Snyder | 128/80 C UX |
| 2,179,903 | 11/1939 | Spears | 128/80 C |
| 2,467,907 | 4/1949 | Peckham | 128/80 C |
| 2,877,033 | 3/1959 | Koetke | 128/80 F X |
| 3,533,651 | 10/1970 | Prahl | 128/80 F X |
| 3,799,159 | 3/1974 | Scott | 128/80 C |
| 3,817,244 | 6/1984 | Taylor | 128/80 C |
| 3,901,223 | 8/1975 | May | 128/80 F |
| 3,902,482 | 9/1975 | Taylor | 128/80 C |
| 4,088,130 | 5/1978 | Applegate | 128/80 F |
| 4,139,002 | 2/1979 | Almedia | 128/80 C |
| 4,245,629 | 1/1981 | Cummins | 128/80 C |
| 4,249,524 | 2/1981 | Anderson | 128/80 C |
| 4,271,831 | 6/1981 | Deibert | 128/80 C |
| 4,320,747 | 3/1982 | Daniell, Jr. | 128/80 C |
| 4,337,764 | 7/1982 | Lerman | 128/80 F |
| 4,353,361 | 10/1982 | Foster | 128/80 C |
| 4,361,142 | 11/1982 | Lewis et al. | 128/80 C |
| 4,372,298 | 2/1983 | Lerman | 128/80 C |
| 4,381,768 | 5/1983 | Erichsen et al. | 128/80 C |
| 4,493,316 | 1/1985 | Reed et al. | 128/80 C |
| 4,503,846 | 3/1985 | Martin | 128/80 C |
| 4,506,661 | 3/1985 | Foster | 128/80 C |
| 4,520,804 | 6/1985 | DiGeorge | 128/80 C |
| 4,603,690 | 8/1986 | Skeen | 128/80 C |
| 4,637,382 | 1/1987 | Walker | 128/80 F X |
| 4,655,201 | 4/1987 | Pirmantgen | 128/80 C |
| 4,697,583 | 10/1987 | Mason et al. | 128/80 C |
| 4,781,180 | 11/1988 | Solomonow | 128/80 C |

FOREIGN PATENT DOCUMENTS 841190 6/1952 Fed. Rep. of Germany ........ 623/39

OTHER PUBLICATIONS

Jack L. Lewis, Ph.D., et al., "A New Concept In Orthotics Joint Design-The Northwestern University Knee Orthosis System", Orthotics and Prosthetics, vol. 37, No. 4 (Winter 1983-1984), pp. 15-23.

Jack L. Lewis, Ph.D., et al., "A New Concept in Orthotics Joint Design-The Northwestern University Knee Orthosis System Part II: The Complete Orthosis", Orthotics and Prosthetics, vol. 38, No. 1, (Spring, 1984), pp. 13-28.

William D. Lew, M. S., et al., "A Comparison of Pistoning Forces in Orthotic Knee Joints," Orthotics and Prosthetics, vol. 36, No. 2 (Spring, 1984), pp. 85-95.

Tammy K. Inglehart, "Strength and Motor Task Performance as Effected by the Carbon Titanium Knee Brace in Normal Healthy Males," Tammy K. Inglehart (1985).

Michael J. Skyhar, M.D., Patrick W. Cawley, O.P.A.,

(List continued on next page.)

Primary Examiner—Edgar S. Burr
Assistant Examiner—Moshe I. Cohen
Attorney, Agent, or Firm—Knobbe, Martens, Olson & Bear

[57] ABSTRACT

A knee orthosis is disclosed providing forces approximating the forces exerted by predetermined knee ligaments; and which further protects against hyperextension, more specifically, the knee orthosis of the present invention provides a hinge having three members extending from a central portion, two extending upwardly and attached to the leg above the knee and one member extending downwardly and attached to the leg below the knee. During the last 15° to 45° of extension, the hinge, through these three members, exerts an increasing force to the anterior of the tibia proximate to the knee, so that during these critical angles of rotation the tibia may be maintained in its proper position with respect to the femur.

37 Claims, 4 Drawing Sheets

OTHER PUBLICATIONS

R.T. "Clinical Evaluation of the 4-Point ACL Brace (A Preliminary Report of Phrase One)".
Brochure entitled "4 Point ACL or PCL Knee Brace," by Donjoy.
Brochure entitled "The ACL Dilemma-the Townsend Design," by Townsend Industries, Inc.
Article entitled "The Geo-Tibial Knee Orthosis," by Carl Patrnchak, RPT Co.
Brochure entitled "MKS II Marquette Knee Stabilizer," by Frontier Technology, Inc.
Brochure entitled "The OTI Brace," by Orthopedic Technology, Inc.
Brochure entitled "The Polyaction Knee Orthosis," by Scott Orthotics Labs, Inc.
Brochure entitled "The Premiere Knee Support System," by Truform Orthotics & Prosthetics.
Brochure entitled "Lerman Multi-Ligamentus Knee Control Orthosis," by United States Manufacturing Company.
Article entitled "The Lower Limb," *Orthotic Components and Systems*, pp. 216-217.
Brochure entitled "The Analog Knee Orthosis," by Becker Othopedic Appliance Co., copyright 1985.
Brochure entitled "Nuko the Nu-Knee Orthosis", by Camp International, Inc.

KNEE ORTHOSIS

BACKGROUND OF THE INVENTION

The knee orthosis of the present invention relates to orthotic devices generally, and specifically to a knee orthosis designed to allow normal range of knee movement while simultaneously providing protection against injury that may be caused by hyperextension or other harmful stresses to the knee joint.

The great increase in the popularity of sports, both recreational and professional, has brought about an increase in the number of sports-related injuries suffered by participants in such activities. Knee injuries, specifically, are common in many sports activities, particularly those requiring running and jumping; affecting weekend sportsmen as well as professional athletes. For example, in sports such as basketball and gymnastics, the knee is subject to the inevitable stress of jumping and landing in awkward or unusual positions which may result in injury and a weakening of the knee. In other sports, knee injuries are similarly common. For example, a football player may fall on an opposing player's fully extended knee or otherwise apply force to the knee structure in a manner and at an angle for which it is not designed, after which the knee may be severely, or even permanently damaged.

During normal movement, the major bone structures proximate to the knee joint rotate within approximately one plane during extension and flexion of the knee. More specifically, these bone structures move in a plane anterior-posterior (front-back) to the body, although there is some medial or lateral (inside or outside) movement, depending upon the knee's activity.

In medical terms, the movement of the knee may be defined as a rotation between the femur (the thigh bone), and the tibia (the shin bone). In flexion, or the flexing of the joint, the tibia rotates toward a smaller angle with the femur. The contrary movement is extension, where the tibia rotates with respect to the femur toward full extension, which is the straightening of the leg. The condyle or articulating surface of the tibia is generally symmetrical, while the condyle of the femur includes an oblong epicondyle with a bone prominence on the posterior side.

At full flexion the tibia rests against the posterior of the femoral epicondyle, creating an overall lengthening of the leg. As the knee begins extension, the tibia travels about a more rounded portion of the femoral condyle, and continues about a progressively flatter portion. Therefore, during rotation toward extension, the respective relationship between the tibia and femur changes because of the change in shape of their adjacent articulating surfaces. As a result, there is an overall shortening of the leg. Specifically, the tibia tends to slide anterior with respect to the femur, and there is an overall shortening of the leg, both of which effects are especially significant during the last 30° of extension. During flexion the reverse is true, i.e., the tibia slides posterior with respect to the femur and the leg becomes longer overall.

To constrain the knee within this range of motion, several ligaments connect the femur with the tibia. Two ligaments are of particular importance; one, the anterior cruciate ligament (ACL), and two, the posterior cruciate ligament (PCL). Generally, the ACL works to prevent the tibia from gliding off the front of the femur during extension and the PCL prevents the tibia from gliding off the rear of the femur during flexion.

One common type of knee injury associated with hyperextension involves damage to the anterior cruciate ligament, which connects the anterior of the tibia with the posterior of the femur. When the ACL is deficient or destroyed, the tibia, during extension can move anteriorly from its anatomically preferred position. An ACL deficiency is a serious problem. In addition to the pain and discomfort caused by injury to the ACL, the misalignment of the joint subjects other ligaments, cartilage, and support structures to increased loads which they were not intended to bear. For this reason, injuries to the ACL are often associated with damage to the medial meniscus cartilage, which can be pinched between the femur and the misaligned tibia. Also due to the misalignment, ACL damage is often accompanied by stretching of the collateral ligaments of the knee, particularly on the lateral side.

In each individual knee injury case, a ligament, or cartilage, or combination of ligaments and cartilage may be damaged. Also, the extent of the damage to any of these knee structures may vary. Accordingly, the recommendation for rehabilitation or healing of the knee may vary depending on the extent and nature of the particular injury suffered by the individual.

Generally, two options are available to those suffering knee injuries of this type: (1) reconstructive surgery, or (2) attempting to rehabilitate the knee through programmed exercise, and the natural healing process. Another option, contraindicated in almost all cases, is the immobilization of the knee for any extended period of time. Such immobilization may in fact be harmful to the healing process, as well as being impractical for day to day life. In addition, a doctor's recommendation that the injured person simply curtail his activities is often not realistic, due to the strong likelihood that the injured person has led an active lifestyle prior to injury and will, in many cases, continue his or her sports activities despite the physician's warning of the risk of further injury.

As stated above, immobilization of the knee for extended periods of time has been shown to have an overall negative effect on the process of healing most injuries commonly sustained by the knee. Conversely, the exercise of an injured knee, in a natural or even programmed manner, often may have very positive effects in the healing of many types of knee injuries. One particular problem overcome by continued exercise is the formation of adhesions, which are defined as "the union of bodily parts by growth." In a nonmoving or immobilized knee, adhesion may occur between the knee joint and cartilage or between the knee bones themselves, among other possibilities. Mobility of the knee joint during the healing process has been proven in clinical studies to reduce the formation of adhesions. Adhesions are particularly troublesome in patients electing reconstructive surgery, and to a lesser extent, the adhesion problem also affects patients not electing surgery.

After sustaining a knee injury of any type, a patient may choose not to submit to surgery for many reasons, including the nature and extent of the injury, his or her medical history, inadequate financial resources, or an unwillingness to undergo a typically protracted convalescence. For those patients not electing surgery, it is extremely desirable to provide the type of knee support that may be provided by an effective orthosis, in order to prevent further injury and to allow the healing process to proceed normally. For certain severely injured patients, a simple, everyday activity such as walking down a flight of stairs may pose the potential for a damaging injury, thereby making the support afforded by an effective knee orthosis a virtual necessity. With a less severely injured knee, an athlete with an effective orthosis may be able to continue physical activity that would not be possible or would be dangerous without the protection afforded by such a knee orthosis.

Even if surgery is chosen, there is need for an effective orthosis. The postoperative knee is typically very weak immediately after surgery. Therefore, for a postoperative knee, an effective orthosis is at least useful, and possibly mandatory in order to protect the repaired structures during the time required for healing. At the same time an effective knee orthosis must allow mobility of the postoperative knee to avoid the above-discussed problem of formation of adhesions, as well as to avoid a number of other problems associated with knee immobility. Furthermore, the natural and normal range of movement is often essential to the proper rehabilitation of the postoperative knee, and thus there is a need for an effective orthosis which allows natural movement while protecting the healing structure.

Therefore, a knee orthosis has been shown to be an extremely useful and sometimes necessary device for a patient suffering an injured knee, whether or not surgery is chosen. An orthosis which can selectively protect the newly repaired ligament or the damaged or weak ligament, while allowing an adjustable range of motion, would greatly advance the rehabilitation process.

Currently, knee orthoses are available which address many of the different types of injuries that may be sustained by the knee, however, none has been able to achieve 100% protection while simultaneously allowing 100% of the normal movement of the knee. In other words, there is always a trade-off between restriction of movement and protection of the damaged knee structure. In addition, some knee orthoses are more effective at correcting specific injuries. For example, an orthosis directed to a knee with a damaged ACL requires force compensation to the anterior of the tibia, while an orthosis for a damaged PCL requires force compensation to the posterior of the tibia. In general, an effective knee orthosis should apply force in such an amount and direction so as to compensate for the function of the damaged knee structures, while simultaneously permitting the largest possible range of movement to the affected knee.

The prior art encompasses many knee orthotic devices. A knee orthosis typically comprises two hinges, one located on the medial (inner) side and the other on the lateral (outer) side of the knee. The orthosis also must include some structure for attaching each of the hinges to the leg, both above the knee and below the knee.

The simplest prior art hinge comprises a single pivot axis, positioned approximately in the middle of the range of motion of the knee. Many such single axis knee orthoses are commercially available.

However, as discussed previously, the actual motion of the human knee does not follow a single pivot point. Rather, during approximately the last 30 degrees of extension, the tibia rolls anteriorly with respect to the femur as much as 8 millimeters, due to the structure of the adjacent contacting surfaces of the femur and the tibia at the knee joint. In addition to the anterior motion of the tibia during extension, the overall length of the leg shortens due to the traveling of the tibia along the posterior condoyle of the femur. Therefore, a leg is at its shortest during full extension, and longest at full flexion.

This shortening of length creates problems for the user of a single axis knee orthosis because such an orthosis cannot lengthen or shorten its overall length. For example, if such an orthosis is securely fastened both to the upper leg and the lower leg at full extension, and then the leg is rotated in flexion, the orthosis cannot become longer like the leg. As a result, in this example, the single axis knee orthosis creates forces pushing the tibia and femur together. This effect, typical of a single axis knee orthosis is commonly termed "pistoning" in the orthotics profession. In many cases, the use of a single axis knee orthosis may actually aggravate the existing injury, or may even increase the risk of other types of knee injury, due in part to the pistoning effect.

Another problem with the single axis knee orthosis is termed "migration" which is also associated with the lengthening and shortening of the leg during flexion an extension. Migration is the partial dislocation of the orthosis due to lengthening and shortening of the leg. Such dislocation, or migration, reduces the effectiveness of the orthosis to protect the injured knee structure, and may contribute to other types of knee injury. In addition, migration may result in lack of comfort to the wearer caused by a loosely fitting knee orthosis that slides about during use.

The polycentric hinge is one type of hinge that has been developed to address the problems of pistoning and migration. A polycentric hinge comprises two fixed pivot points connected by a rigid structural member. Extending outward from each of the two fixed pivot points is another rigid member. Each end remote from the hinge is attached rigidly to the leg respectively above and below the knee. A polycentric hinge is somewhat more effective at avoiding the pistoning problem of the single axis hinge, as it allows for some shortening and lengthening of the knee orthosis in accordance with the shortening and lengthening of the leg. However, such an orthosis is not controllable as to the position in which shortening and lengthening occurs, therefore lacking precise control of the orthosis throughout flexion and extension.

Another disadvantage of the polycentric hinge, common with that of the single axis hinge, is the abrupt halt of the hinge mechanism at the end of extension. In other words, when the knee orthosis reaches full extension, further extension is abruptly halted, transmitting a shock to the knee, which can cause further damage to the already injured knee. In more physical terms, the leg can develop a substantial rotational momentum during extension, which will be partially absorbed by the knee structure which can result in injury to the knee and its surrounding structures.

Other prior art devices designed to simulate motion of the knee include a hinge similar in shape to a cross section of the knee joint, and held together by straps simulating the corresponding ligaments of the knee, described in U.S. Pat. No. 4,361,142 to Lewis et al. Such a hinge consists of a metal, multicurved femoral member in the shape of the sagittal profile of the femur proximate to the knee joint, and a slotted tibial component with a larger, flatter articulating surface approximating the profile of the proximate tibia. Such a hinge approximates the natural motion of the knee, and when inextensible dacron "ligament" straps are connected between the members in various configurations, an approximate model of the knee, complete with restricting ligaments, is established, which is then connected to the body by means of two rigid side bars.

In the device described in the Lewis patent, as in many others, the application of pressure to the various points in the knee, or "loading," is accomplished at or proximate to the hinge and is transmitted to the upper and lower leg, respectively, through a rigid member attached nonrotatably to the upper and lower leg. As a result, such transmittal of force through a rigid member results in a rotation of the orthotic structure affixed to the upper and lower leg, thereby translating to a force applied to the leg via the edge of the orthotic structure. As a result of this edge pressure, there is often an uneven distribution of force throughout the assemblies affixed to the leg both above and below the knee, resulting in discomfort and inefficiencies of the knee orthosis.

In general, it should be remembered that the motion of the knee joint is much more complex than a rotation about a fixed axis and, as shown above, the motion of any knee orthosis is intrinsically less complex than the natural knee motion. Therefore, when a real orthosis is affixed on the leg, there is an inherent conflict between the natural joint structure and the knee orthosis as the orthosis attempts to force the knee to follow its simplified motions. The goal of the knee orthosis designer is to reduce this inherent conflict as much as possible while at the same time providing a restraining force at predetermined limits of motions. These constraints should ideally be introduced in a direction, amount, and location to compensate for the specific knee insufficiency.

However, when such constraints are introduced, their implementation may present a potential for other types of knee injury. For example, as previously discussed, the user of some prior art knee orthoses will encounter an abrupt halt at the end of extension. This abrupt halt, whose severity is increased if the leg has built up substantial momentum in extension, may translate to a substantial shock to the knee and its surrounding structures. In general, the constraint forces of the prior art devices are usually introduced abruptly, at a location proximate to the hinge from which these forces are then translated through a rigid member to the adjacent leg structures. Therefore, it would be an improvement in the art to provide a device which gradually applies an increasingly greater constraint force to avoid the shock that can be encountered when the prior art devices apply constraint forces. It would be a further improvement if the force, or "loading" of the knee orthosis is directly applied proximate to the bone structure where needed to compensate for a particular injury.

For example, in injuries to the ACL, the structure of the knee, together with the momentum building up in the extending leg, create an increasingly substantial force in extension which can move the tibia anteriorly off the femur, misaligning the joint and thereby causing a potential for injury to other knee structures. Therefore, it can be seen that it would be an improvement in the art to provide an orthosis to compensate for an ACL injury by applying an increasing force during extension to properly align the tibia with respect to the femur. It would be a further improvement if such a knee orthosis were to apply constraint forces directly to the structures surrounding the knee, so that the increasing constraint force counteracts the anterior forces on the tibia, thereby providing substantial protection to the ACL deficient knee. It would be a still further improvement if such a knee orthosis could avoid the previously discussed problems of pistoning and migration, by shortening during full extension and lengthening during flexion.

Finally, the effective prior art devices operate in a single plane throughout extension. For example, the single axis hinge and the polycentric hinge are both constrained to move in a single plane by the nature of their connections. Therefore, these prior art orthoses allow only knee movement within this one plane, while the natural motion of the knee, although moving generally in one plane, actually moves in three dimensions and rotates about its axis, if permitted. It is of interest that, in general, the rotary ligaments of the knee are the controlling factors of three dimensional motion. The excursions of the joint from the single plane are generally small and depend upon the activity the knee is supporting. Although such excursions are small they are substantially not permitted by prior art devices that have a fixed axial structure, such as a single axis knee orthosis. Therefore, if the rotary ligaments are not damaged, then in many cases the prior art orthoses restrict movement unduly.

Therefore, it would be an improvement in the art to provide such a device that allows a slight rotary movement of the tibia with respect to the femur, so as to permit a more natural movement of the knee joint.

BRIEF SUMMARY OF THE INVENTION

The present invention provides a knee orthosis that can apply a constraint force in a novel manner to compensate for deficiencies in the knee structure. This constraint force is applied in a gradually increasing amount to properly guide the knee articulation throughout its motion and to gradually slow and eventually stop the extension of the knee at a predetermined angle of extension. In order to enhance effectiveness of the constraint force, as well as to enhance comfort and wearability, the application of force (or "loading") of the knee orthosis is accomplished away from the hinge and proximate to the portions of the femur and the tibia where needed to effectively compensate for the deficient knee. A slight degree of rotational movement about the axis of the leg is permitted in order to accommodate a substantially natural extension and flexion of the leg.

In particular, the present invention comprises an upper orthotic assembly attaching to the leg above the knee, a lower assembly attaching below the knee, and two articulating hinge assemblies, one on the medial (inner) side of the knee, and the other on the lateral (outer) side. Each hinge assembly has one lower member rotatably attached to the hinge at a single axis pivot point, and rigidly affixed to the lower assembly. Further, each hinge assembly has two upper members rotatably connected to the upper assembly. The two upper members constrain the hinge to move within an arcuate path defined by their rotation about their respective pivot points on the upper assembly. As the hinge rotates within this arcuate path, the single axis pivot point, being structurally connected, also moves. For example, in extension as the path of the lower arm moves in an anterior direction, the hinge rotates generally posterior, while the single axis pivot point moves posterior and upward, causing a shortening of the orthosis, as well as applying force to restrain the tibia against anterior movement.

The hinge is constructed so that it acts as a single axis hinge beginning at full flexion and continuing until somewhere between 45° and 15° short of full extension and preferably 30°. Beyond this selected angular position the knee orthosis begins to get shorter as described above, and applies an increasing force to structures proximate to the knee, including the anterior of the tibia proximate to the knee joint, the posterior of the femur proximate from the knee, and the anterior of the femur remote from the knee. Therefore, as the knee articulates in flexion and extension, the tibia is forced and restrained into the proper relationship with respect to the femur. The result for the user is that the orthosis compensates for an ACL weakness by application of force to the bone structures proximate to the knee during extension or flexion, thereby allowing a safe, normal range of movement to an ACLdeficient knee.

Furthermore, extension is inhibited when the increasing force acting against extension becomes greater than the force applied toward extension. This application of increasing force is a substantial advantage because the extending leg decelerates smoothly to a full stop, unlike other devices which cause an abrupt stop at full extension. Therefore, with the present invention, there is less chance of damage to the knee joint due to the jarring or shock upon the knee orthosis attaining full extension. This feature of the present invention, when compared with other devices, produces a more natural application of force restraining the knee joint, is safer for movement of the knee, and provides for better healing of an injured or deficient ligament.

Also, the lengthening of the knee orthosis, as the leg becomes longer in flexion, significantly reduces potentially damaging pistoning forces. At the same time, the problem of migration, or a slippage of the knee orthosis, is significantly reduced due to the absence of forces pushing or pulling the leg attachment assemblies away from their desired position. As an added advantage, the lack of migration renders the knee orthosis much more comfortable to the wearer.

Thus, in general, the knee orthosis of the present invention applies force proximate to the knee as needed to correct for an ACL deficiency. Specifically, forces are transmitted from the hinge directly to the two rotation points on the upper assembly, and to the lower assembly through the lower member. This method of applying pressure provides a more comfortable and effective knee orthosis, because it reduces excessive edge pressure by applying force to an entire area rather than to a particular point.

Additional embodiments of the invention may include features permitting adjustability of the amount of force applied against the tibia during extension. Other embodiments may also include adjustability of the angle at which the increasing force begins to be applied. Many other adjustable features may be provided, including an adjustable amount of upward movement and shortening of the knee orthosis, or an adjustable amount of posterior movement. Also, an alternative embodiment may bias the motion of the arcuate path in a certain direction.

These and other advantages and features of the present invention will become more fully apparent from the following description and appended claims taken in conjunction with the accompanying drawings. CL BRIEF DESCRIPTION OF THE DRAWINGS

DETAILED DESCRIPTION OF THE PREFERRED EMBODIMENT

The invention is best understood by reference to the figures wherein like parts are designated with like numerals throughout.

Figures 1, 2:
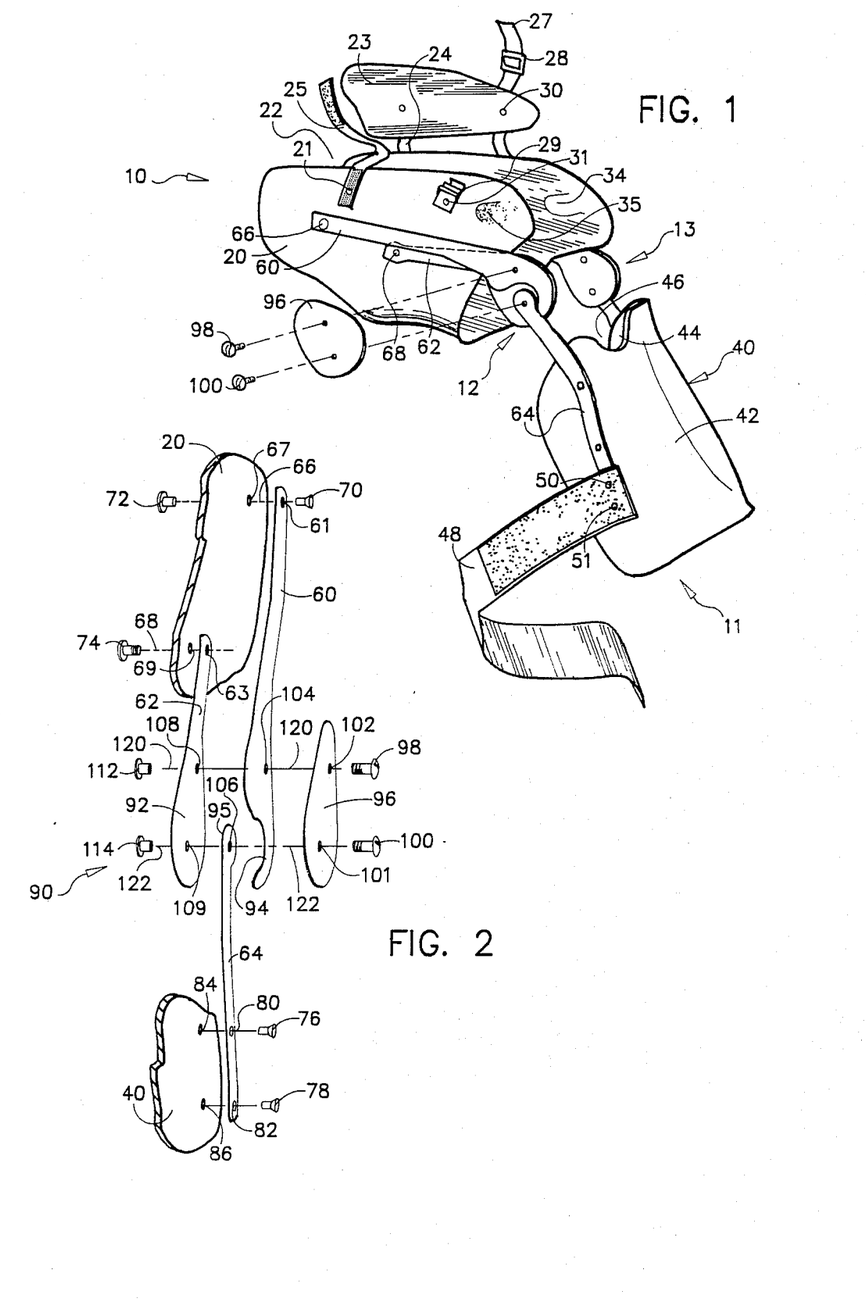
FIG. 1 is a perspective view of a preferred embodiment of the knee orthosis of the present invention showing an exploded view of a portion of the hinge.
FIG. 2 is an exploded view of the hinge assembly of the present invention.

The knee orthosis of the present invention is shown in perspective in FIG. 1. Generally, the knee orthosis comprises an upper orthotic assembly 10, a lower orthotic assembly 11, and two hinges, one on each opposing side of the knee, specifically, a lateral hinge 12 and a medial hinge 13. The two hinges are identical in structure and operation, except that one is the mirror image of the other. It should be clear that since each hinge is the mirror image of the other that a structure and function applicable to one hinge is equally applicable to the other mirror image hinge.

The upper orthotic assembly 10 includes apparatus for attachment of the knee orthosis to the portion of the leg above the knee. Similarly, the lower orthotic assembly 11 includes apparatus for attachment to the lower portion of the leg below the knee. Advantageously, the upper orthotic assembly 10 and the lower orthotic assembly 11 have the structure described herein. However, it should be understood that many different orthotic structures and apparatus for attachment may be capable of providing substantially the same functions.

The upper orthotic assembly 10 comprises an upper shell 20 made of a resilient hard plastic material, and preconformed to the shape of the leg above the knee by methods well-known in the field of orthotics, advantageously by the technique of vacuum-formed polypropylene described in the following paragraph. The upper shell 20 defines an interior opening 22 through which the upper portion f the leg may be inserted. Anterior plate 23 is designed to fit within opening 22 to thereby provide a structure for attaching the upper shell to the upper portion of the leg. The anterior plate 23 may be comprised of a similar hard plastic material and may likewise be conformed to the portion of the leg to which it abuts by means well-known in the field of orthotics.

The technique whereby a plastic shell is created to conform with the leg, common in the art, is briefly outlined in this paragraph. First, a positive cast of the patient's leg is formed in any well known manner. A nylon interface material may be wrapped around the outside surface of the positive cast. A sheet of polypropylene (3/16" is a typical thickness) is heated till clear and then wrapped around the nylon interface material. The polypropylene is then sealed at all edges and a vacuum hose is inserted into the space between the cast and the polypropylene. As a vacuum is applied, the polypropylene is "pulled" into a shape that conforms with the patient's leg. After cooling, the polypropylene may be cut to the desired shape for attachment to the patient's leg.

The anterior plate 23 is held in position by medial plate strap 24 on the medial side, and lateral plate strap 25 on the lateral side. Each of these straps may be affixed to upper shell 20 by any suitable means, for example, strap 25 is affixed to upper shell 20 by means of rivet 21. Each of these straps passes through an upper plate clasp 26 (shown in FIG. 3). Each such strap 24, 5 comprises at opposite ends, male and female velcro sections so that each respective strap 24, 25 may pass through the clasp 26 and be placed back over itself onto the complementary velcro portion, thereby accommodating a firm, but adjustable attachment of the upper portion of the anterior plate 23 to the upper shell 20.

Lower plate strap 27 is affixed to the anterior plate 23 in any well-known manner, for example, by rivet 30 passing through a portion of lower plate strap 27 in anterior plate 23. Similarly, lower lateral clasp 29, and the lower medial clasp (not shown) are attachable to the upper shell in any well-known manner, for example, lower lateral clasp 29 is attached by rivet 31 passing through clasp 29 and the upper shell 20.

The lower portion of anterior plate 23 is affixable to upper shell 20 by connection of lower plate strap 27 to lower lateral clasp 29 in any well-known manner, advantageously by connection of strap clasp 28 to lower lateral clasp 29. Lower plate strap 27 may be comprised of an elastic material, and is threaded through openings in strap clasp 28, so that strap clasp 28 is adjustable about the length of lower plate strap 27 in any well-known manner. Strap clasp 28 is affixable to lower lateral clasp 29 in any well-known manner, advantageously by snapmating a portion of strap clasp 28 to clasp 29. On the medial side of lower plate strap 27, a similar strap clasp (not shown), and a similar lower medial clasp (not shown) is provided to similarly attach lower plate strap 27 to upper shell 20.

In order to enhance proper fit, and to prevent unwanted movement of the upper shell 20, medial supracondylar grip 34, and lateral supracondylar grip 35 are advantageously provided on the lower portion of upper shell 20 to help bind the shell in place with respect to the knee. Both supracondylar grips 34, 35 comprise smooth, substantially spherical indentations in the upper shell 20, the indentations facing inward so that when the upper shell 20 is affixed to the leg the indentations contact the leg just above, and proximate to, the knee joint.

Lower orthotic assembly 11 comprises, generally a lower shell 40, which in turn comprises an outer shell 42 made of a hard plastic material, such as polypropylene and an inner surface 44 comprised of a softer, resilient closed-cell foam material such as that produced under the brand name of "Plastizote."

Lower shell 40 is preconformed to the portion of the leg below the knee by any means known in the art, such as the vacuum-formed polypropylene method previously described, with an additional step included so that a piece of the closed cell foam material is wrapped around the positive cast before the polypropylene is applied and then the polypropylene is pulled directly over the foam material.

The posterior portion of lower shell 40 defines an opening 46 through which the lower portion of the leg may be inserted. To secure the leg across opening 46, a lower shell strap 48 is provided. At one end, lower shell strap 48 is affixed to lower shell 40 in any well-known manner, for example, by rivets 50 and 51 affixed through strap 48 and lower shell 40. On the other side, a metal strap ring (not shown) is affixed to the shell on the opposite side proximate to the edge in any well-known manner as, for example, by a rivet affixing a flexible cloth connector which surrounds the ring, so that lower velcro shell strap 48 may pass through the ring. Lower shell strap 48 may be comprised of complementary velcro material so that after lower shell strap 48 passes through the strap ring (not shown) the strap may be returned and affixed to itself, thereby to provide a snug, but adjustable, fit. The strap ring (not shown) may be affixed to lower shell 40 by wellknown means, such as a rivet (not shown).

Referring both to FIGS. 1 and 2, medial hinge 13 (and likewise, lateral hinge 12) comprises a long upper member 60, a shorter upper member 62 and a lower member 64. The long upper member 60 may be comprised of, for example, a metallic material, advantageously, surgical steel, and has a shape generally flat on each side throughout its length. At the remote end of upper member 60 where it attaches to the upper shell 20, upper member 60 is rotatably connected at high pivot point 66 defined on upper shell 20. Similarly, the shorter upper member 62 comprises a metallic material with a structure generally flat on each side. At its connection to upper shell 20, shorter member 62 is rotatably connected at low pivot point 68 defined on upper shell 20. Referring specifically to FIG. 2, the rotatable connection between upper member 60 and upper shell 20 comprises, for example, a pivot screw 70 passing through hole 61 defined on the remote end of longer upper member 60 and continuing through the line defining high pivot point 66 through hole 67 defined on upper shell 20, and matably attached to pivot nut 72 which is threaded on its inner diameter.

Pivot nut 72, like all pivot nuts described herein, comprises a smooth cylindrical shape on its outside diameter, and is threaded on its inside diameter. The head of the pivot nut may slideably rest against a flat surface and the body may extend through a hole in that surface. Its threaded inner diameter may mate with a threaded screw positioned on the other side of the flat surface and, therefore, when installed, the head of the pivot nut rests against a surface on one side and the head of the pivot screw rests against the surface on the other side, in effect sandwiching the middle surfaces. As a result, each respective component through which a pivot nut passes may rotate annularly about the diameter of the pivot nut.

Shorter upper member 62 may be attached to upper shell 20 by, for example, a pivot screw 74 passing through hole 69 defined on upper shell 20, and continuing along the line defining lower pivot point 68 and mating with threaded hole 63 defined on the remote end of shorter upper member 62. In the disclosed embodiment, lower member 64 is nonrotatably attached to lower shell 40 by means of, for example, rivets 76, 78 extending through holes 80, 82 on the remote end of lower member 64 and continuing through holes 84, 86 in lower shell 40.

In FIG. 2, the central portion of the hinge is shown generally by arrow 90, and the members 60, 62, and 64 each have an end proximate thereto, and an end remote therefrom. Proceeding from left to right, the proximate end of the shorter upper member 62 comprises a flat surface with a shape generally approximating that of a tear drop 92. The proximate end of longer upper member 60 comprises two flat surfaces, on each side, with the approximate C-shape 94. The proximate end of lower member 64 comprises two flat surfaces, with a rounded outer edge 95. Hinge plate 96 is approximately flat on the surface adjacent to the proximate ends of longer upper member 60 and lower member 64. Hinge plate 96 may be comprised of, for example, a metallic material which may, advantageously, be surgical steel. To rotatably maintain the components of the central portion 90 of the hinge in their proper relations, pivot screws 98, 100 are provided to pass through the hinge and mate with pivot nuts 112, 114. Specifically, the outer diameter of pivot nut 112 passes from the left along line 120 through a hole 108, hole 104 and hole 102, and matably engages pivot screw 98, so that longer upper member 60 may rotate with respect to shorter upper member 62 and hinge plate 96. The connection along line 120 defines what will be referred to as the "upper pivot point 120."

Similar means are provided to affix the lower portion of the proximate end 90 of the hinge to the lower member 64. Specifically, third pivot nut 114 passes from the left along line 122 through holes 109, 106 and 101, and mates on its inner diameter with third pivot screw 100. In the disclosed embodiment, each of the holes 109, 106, 101 freely permit rotation of their respective members about the outer diameter of pivot nut 114, but in other embodiments, the shorter upper member 62 and the hinge plate 96 may be fixed to the pivot nut 114, the lower member 64 being rotatable about pivot nut 114. The connection along line 122 between pivot nut 114 and pivot screw 100 will be referred to as the "single axis pivot point 122", for reasons which will be explained later.

Figures 3, 4:
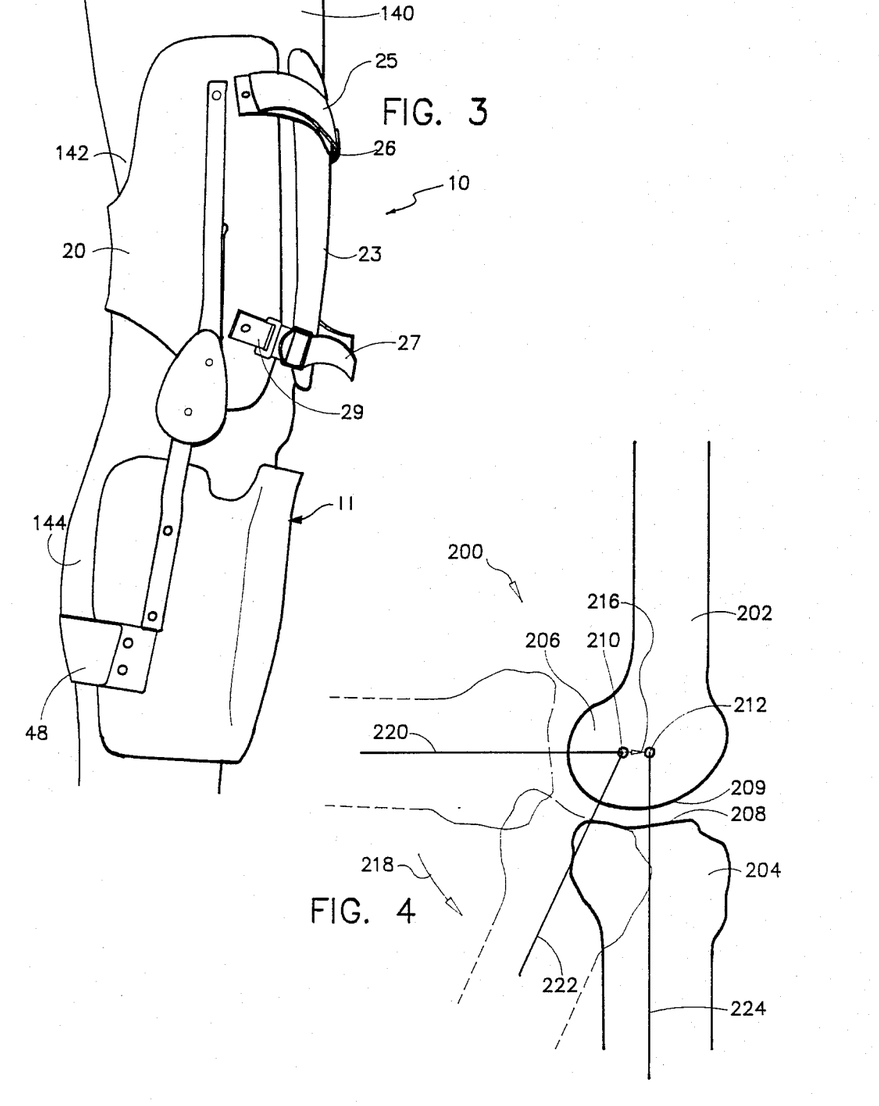
FIG. 3 is a perspective view of the knee orthosis affixed to a leg at full extension.
FIG. 4 is a schematic view of the femur and tibia in various alignments from flexion to full extension, illustrating the movement of the axis of rotation occurring while the knee is articulating.

To better illustrate the manner in which the upper orthotic assembly 10 and lower orthotic assembly 11 are affixed to a leg, FIG. 3 illustrates the knee orthosis of the present invention affixed on a typical leg 140. Note that lateral plate strap 25 is illustrated passing through upper plate clasp 26 on anterior plate 23 and then passing back on to itself where the velcro provides a snug fit. Also note, lower plate strap 27 is affixed to lower lateral clasp 29 on upper shell 20 to provide a snug fit between the assembly 10 and the upper portion 142 of leg 140. Also note that lower shell strap 48 is illustrated passing around the back portion of the calf 144 of leg 140 in order to firmly affix lower assembly 11 to the bottom portion of leg 140.

The preferred embodiment and alternative embodiments will be understood more fully once the operation of the knee orthosis of the present invention is understood. Before undertaking an explanation of the operation of the knee orthosis, it is useful to recall the physics of the motion of the rotating knee. With reference to FIG. 4, the knee structure shown generally at 200 is illustrated rotating in the direction of arrow 218 from a position 220 of flexion, to a position 222 at approximately 30° short of full extension, and finishing at position 224 at full extension. Note that as the tibia 204 rotates from position 220 to 222, the rotation of the tibia 204 with respect to the femur 202 is substantially about a single axis 210. As the extension extends beyond position 222 toward full extension at position 224, the axis of rotation of the tibia with respect to the femur 202 moves along a path indicated generally by arrow 216 and eventually halts at axis 212. This shifting of the axis along arrow 216 is partially caused by the changing relation of articulating surface 208 of the tibia 204 and articulating surface 209 of the femur 202. More specifically, the articular bone prominence on the posterior of the femur, epicondyle 206, is in part responsible for this shift of axis from position 210 to 212. For the purpose of orthotics, and specifically, the knee orthosis, an important effect of this movement is that the knee structure 200 and therefore, the leg (not shown in FIG. 4), becomes shorter overall during this rotation in the direction of arrow 218, particularly during rotation from partial extension position 222 to full extension position 224.

Figures 8, 9:
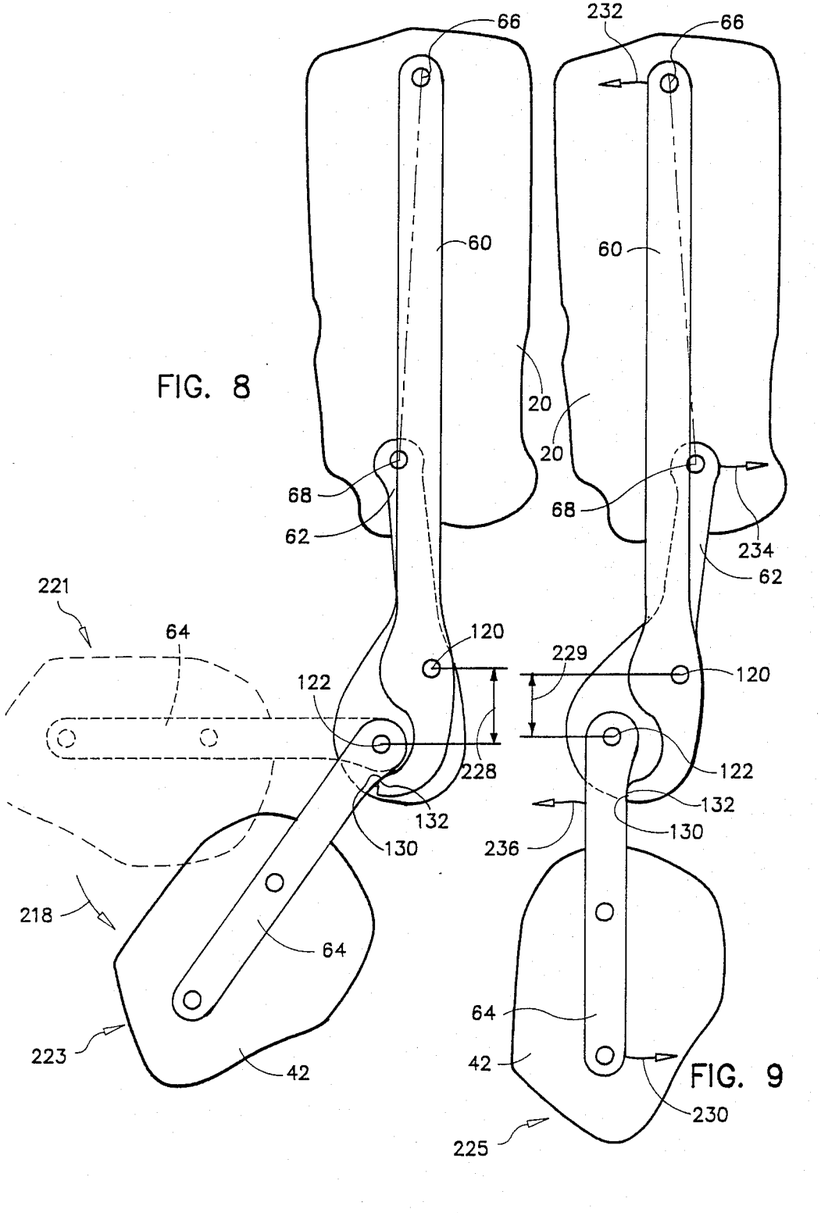
FIG. 8 is a side view of a hinge of the present invention, with the hinge plate removed to disclose the operation of the lower member of the hinge of the preferred embodiment with the lower member moving from a position of flexion, indicated by the dotted lines, to a position within approximately 30° of full extension indicated by solid lines.
FIG. 9 is a side view of a hinge of the present invention with the hinge plate removed to disclose the operation of the hinge of a preferred embodiment, wherein the hinge is in the configuration of approximately full extension.

The operation of the knee orthosis of the present invention and its relationship to the above-described knee rotation can be understood more fully by reference to FIGS. 8 and 9. FIG. 8 illustrates the effect of rotation of lower member 64 from a flexion position 221 in the direction of arrow 218 to position 223, which generally corresponds to a movement of the knee structure 200 of FIG. 4 from position 220 to position 222. In this portion of its arcuate path, the rotation of lower member 64 is substantially about the single axis pivot point 122 which, in FIG. 4, corresponds to axis 210. Referring to FIG. 8, note that upper pivot point 120 is anterior with respect to lower pivot point 68 and that no contact is made between contact surface 132 of lower member 64 and contact surface 130 of long member 60 beyond position 221, in the direction of arrow 218, until lower member 64 is proximate to position 223. As extension continues, the knee orthosis eventually reaches position 225 of full extension as illustrated in FIG. 9.

To illustrate the effect of this extension, a comparison can be made between the configuration of the hinge in FIG. 8 with the configuration shown in FIG. 9. By comparison of four points, specifically, high pivot point 66, lower pivot point 68, upper arm pivot point 120, and single axis pivot point 122, it can be seen in FIG. 9 then that there has been posterior movement of both the upper arm pivot point 120 and single axis pivot point 122 (i.e. a posterior movement of the central portion of the hinge) with respect to low pivot point 68 and high pivot point 66. Also, in FIG. 9 there has been some posterior movement of single axis pivot point 122 with respect to upper pivot point 120, and there has been an overall shortening of the knee orthosis, as can be visualized by a comparison of the vertical length 228 in FIG. 8 with the vertical length 229 in FIG. 9 measured between the same two pivot points. In other words, in FIG. 9, single axis pivot point 122 is now above, and posterior to its position in FIG. 8.

As a direct result, it can be seen that the knee orthosis of the present invention becomes shorter overall during extension similar to the knee structure 200 shown in FIG. 4, thereby substantially preventing the pistoning problem common to other knee orthoses as discussed previously. In addition, the posterior rotation of the single axis pivot point 122 provides a force in the posterior direction.

An analysis of the various forces and vectors causing the shortening of the orthosis and its application of force begins with the assertion, previously discussed, that the rotation of lower member 64 from position 221 in FIG. 8, to position 223 is essentially a single axis rotation about single axis pivot point 122. Then, at position 223 in FIG. 8, contact surface 130 meets contact surface 132, and maintains contact throughout the remainder of extension to position 225 as shown in FIG. 9.

Throughout this latter portion of extension, additional forces are applied to the knee orthosis and thereby to the knee itself. These forces are initially created by the actual extension of the knee and translated through members 60, 62, and 64 to the hinge. More specifically, as extension continues past position 223, further movement toward extension while actually a rotation about single axis pivot point 122, has a major component in a generally anterior direction as visualized by arrow 230 in FIG. 9. This extension force visualized by arrow 230 in turn creates several other forces simultaneously. It is to be remembered that these forces, although treated separately in the following discussion, occur substantially simultaneously.

The first resulting force appears at the high pivot point 66 and is applied in a generally posterior direction as visualized by arrow 232 in FIG. 9. This force is a direct translation of the force applied to extension of lower member 64. Specifically, the contact surface 132 of lower member 64 makes contact with contact surface 130 of upper member 60 which rotates about upper pivot point 120 thereby applying a generally posterior force in the direction of arrow 232 to high pivot point 66.

The second resulting force appears in the direction indicated by arrow 234. In addition to the leverage providing the first resulting force, the single axis pivot point 122 acts as the end of a lever arm using the upper pivot point 120 as a fulcrum to leverage lower pivot point 68 in an anterior direction generally indicated by arrow 234. As a result, the second force appears in an anterior direction, from close pivot point 68. Note that the result of this force can be seen by comparison of the position of the close pivot point 68 with respect to upper member 60 in FIGS. 8 and 9.

The third resulting force is applied to the anterior of the tibia proximate to the knee, in the general direction indicated by arrow 236. Specifically, the generally posterior force applied to single axis point 122 caused by extension force 230 using contact surfaces 130, 132 as a leverage point, is transmitted to the structurally connected upper pivot point 120, causing a generally posterior motion of the central portion of the hinge assembly with respect to lower pivot point 68. As the hinge assembly moves in this generally posterior direction, single axis pivot point 122 travels posterior a greater distance than the contact point between contact surfaces 130, 132, thereby rotating the angle of lower member 64 in the direction indicated by arrow 236. This changing angle effects rotation of the lower member with the result that posterior force is applied to the tibia proximate to the knee.

Figures 5, 6, 7:
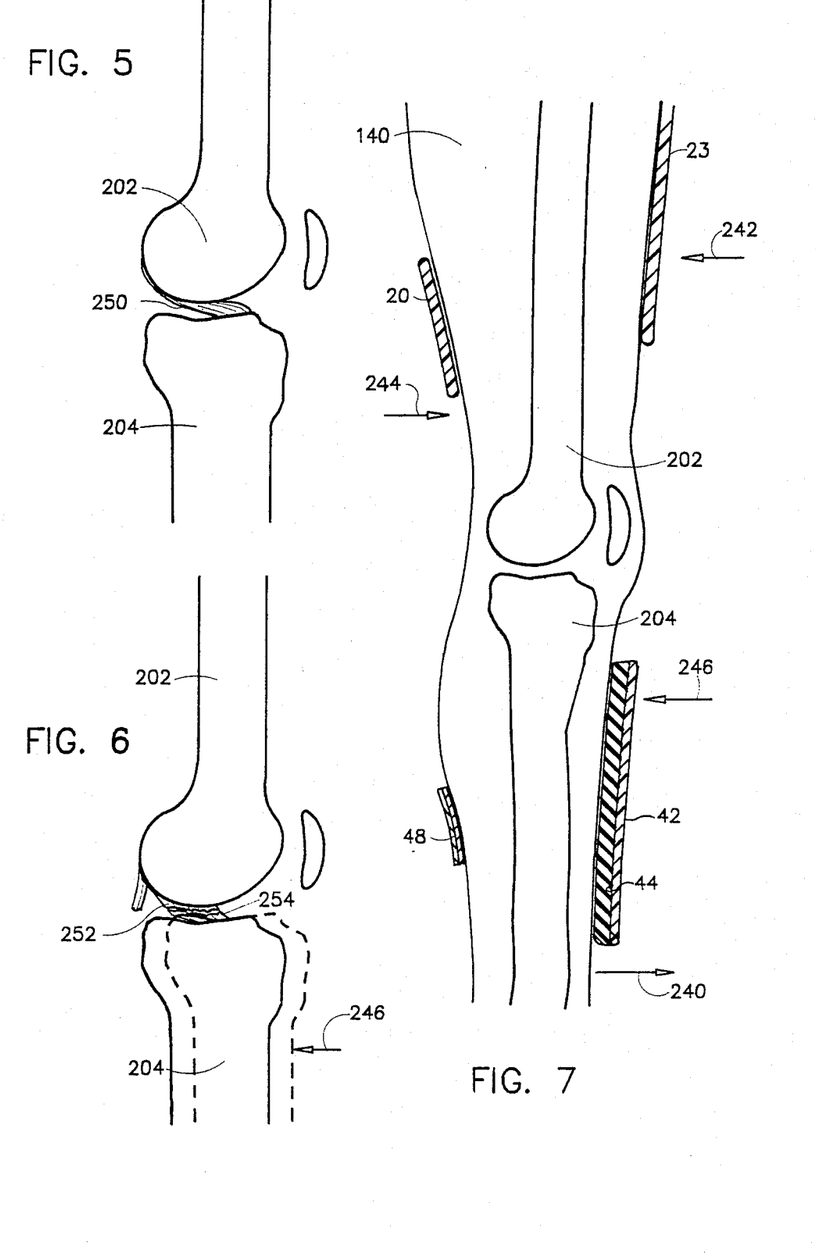
FIG. 5 is a schematic showing of a fully extended knee held in place by a healthy anterior cruciate ligament.
FIG. 6 is a schematic showing of a fully extended knee with a damaged ACL, the dotted lines illustrating the resulting displacement of the tibia with respect to the femur, this displacement being corrected by application of force in the direction indicated by the arrow, causing a relocation of the tibia to the alignment indicated by the solid lines.
FIG. 7 is a schematic showing of a fully extended knee and a cross-sectional view of portions of the upper and lower orthotic assemblies, with arrows indicating three directions of forces applied during extension by the knee orthosis of the present invention.

The effect of application of these forces can be more fully understood by reference to FIG. 7 which is a schematic view of a leg 140 with a cross-section of the knee orthosis of the present invention affixed on the leg 140. The major anterior component of the force applied by the leg in extension is illustrated by arrow 240, the posterior force applied by direct translation to the high pivot point 66 is illustrated by arrow 242, the anterior force translated to lower pivot point 68 is illustrated by arrow 244 and finally, the generally posterior force exerted by the changing angle of lower member 64 caused by movement of the hinge in a posterior direction is illustrated by arrow 246. It should be noted that the posterior force to position the anterior of the tibia indicated by arrow 246 is to some degree buffered by the resilient inner surface 44 of the lower shell 40. Therefore, the anterior of the tibia is not abruptly responsive to forces that may be applied by the orthosis of the present invention, but instead, the tibia is urged toward the proper positioning.

An important advantage of the application of force in this particular manner can be illustrated by reference to FIGS. 5 and 6. FIG. 5 illustrates a healthy knee with tibia 204 restrained from anterior movement with respect to femur 202 by means of healthy anterior cruciate ligament 250. In FIG. 6, the anterior cruciate ligament 250 is damaged, and therefore is shown broken into part 252 and part 254. The dotted lines indicate the mispositioning of the tibia 204 with respect to femur 202 caused by damaged anterior cruciate ligaments 252, 254. The solid lines indicate the proper positioning of the tibia 204 with respect to the femur caused by application of extension force as illustrated by arrow 246 in FIGS. 6 and 7.

The mechanical interactions causing this result may be visualized more easily if, for the purpose of subsequent discussion, we assume that the upper orthotic assembly 10 is maintained rigidly stationary, while the lower orthotic assembly 11 is allowed to rotate freely in extension or flexion. As previously discussed, increasing force begins to be applied as the leg extends from a position approximately 30° of full extension, due to the interaction between contact surfaces 130, 132. While the angle used in the preferred embodiment is 30° the angle may be varied between about 45° to about 15° in order to accomplish the desired result in a particular orthotic environment. As the leg extends further, this interaction causes the central portion of the hinge assembly to rotate in a posterior direction, which in turn causes the top of lower member 64 to rotate posteriorly, as illustrated by arrows 236, 230 of FIG. 9, thereby gradually applying a force opposing the forward movement of the tibia with respect to the femur. This force increases as extension continues and lower member 64 rotates further in the posterior direction of arrow 236.

The above-discussed posterior motion of the hinge assembly also simultaneously causes lower member 64 to be pulled upward as the single axis pivot point 122 rotates upwardly about pivot point 120, thereby resulting in an overall decrease in length of the orthosis to substantially resolve the pistoning problem. As we are assuming that the upper orthotic assembly 10 is stationary, the necessary forces to stabilize the rotation and upward movement of lower member 64 are provided by the interaction between the upper orthotic assembly 10 and both upper members 60, 62. Specifically, these forces are (1) posterior with respect to the remote end of upper member 60, as illustrated by arrow 232 in FIG. 9, and (2) anterior with respect to the remote end of upper member 62 as illustrated by arrow 234. It should be apparent that the gradually increasing force, and the shortening of the assembly, are the result of a series of complex simultaneous interactions between the lower member 64, the two upper members 60, 62, and the hinge assembly itself. As a final note, it should be remembered that the increasing force is not applied as the leg extends from a substantially flexed position as illustrated by position 221 in FIG. 8, toward a predetermined position at approximately 30° of full extension, as illustrated by position 223. The increasing force begins application only when contact is first made between contact surfaces 130. 132.

In the preferred embodiment for the typical ACL injury, the contact between surfaces 130, 132 occurs substantially where the angle, with respect to full extension is, advantageously, 30°. It should be recognized that other angles within the range of 15° 45° may be employed with similar results. However, it is believed that angles in the range of 20° to 35° will be the most effective for use with the orthosis of the present invention. In addition, other angles may be preferred in other embodiments, such as an orthosis designed for an abnormal articulation of the knee. Therefore, within the principles of the present invention, surfaces 130, 132 may make contact at almost any angle of rotation of the knee.

For purposes of illustration the dimensions of one embodiment of the hinge of a knee orthosis of the present invention, for use on an adult male of medium build, are included at this time. As these dimensions are for illustration purposes only, other embodiments may incorporate different dimensions:

| Description | Dimensions |
| --- | --- |
| Long upper member 60: | |
| From high pivot point 66 to upper pivot point 120. | 7½" |
| Radial distance from upper pivot point 120 to contact surface 130. | 2" |
| Shorter upper member 62: | |
| From lower pivot point 68 to upper pivot point 120. | 3¼" |
| From lower pivot point 68 to single axis pivot point 122. | 4¼" |
| Tear drop shape 92: | |
| Width | 2" |
| Length | 2¾" |
| Single axis pivot point 122: | |
| 1" posterior and perpendicular of a line passing from high pivot point 66 through upper member 60 and through upper pivot point 120. | |
| Lower member 64: | |
| From single axis pivot point 122 to closest affixing rivet 76. | 3" |
| From single axis pivot point 122 to furthest affixing rivet 78. | 5¼" |
| From single axis pivot point 122 to contact surface 132. | ¾" to 1" |

In summary then, the knee orthosis of the present invention applies pressure to the leg at at least three points during extension in addition to providing an overall shortening. The knee orthosis of the present invention provides a gradually increasing force against extension, and simultaneously supplies a gradually increasing force to properly position the tibia with respect to the femur, so as to restrict damaging movement of the knee while at the same time allowing substantially normal movement.

In an alternate preferred embodiment (not shown), the upper pivot point may be constrained to an arcuate path that substantially reaches its end point proximate to a predetermined extension, to prevent further articulation of the knee. For example, a mechanical block could be affixed to the upper shell 20 posterior to both upper members 60, 62 and proximate to the hinge, so that further rearward movement of the members 60, 62 is prevented by contact between the block and the respective members 60, 62. As a result, further knee extension is substantially prevented in this embodiment because any further extension would be prevented by the restriction against further posterior movement of the hinge.

Other embodiments (not shown) may comprise a means for biasing each hinge such as, for example, a spring (not shown) connected proximate to the central portion of the hinge 90, between longer upper member 60 and upper shell 20, so that the proximate end of member 60 is biased toward the anterior direction. Such an embodiment would help maintain the proper positioning of each hinge with respect to the knee. Furthermore, such an embodiment may comprise an adjustable biasing means so that the amount of force necessary for extension of the hinge may be varied.

Other embodiments (not shown) may comprise a means for restricting the motion of the upper arm pivot point 120 such as, for example, a solid stop affixed to upper shell 20 anterior to upper member 60 so that its motion, and thereby the motion of the hinge, is restricted.

Other embodiments (not shown) may comprise variations of lengths, positions, and shapes of members 60, 62, and 64. For example, members 60, 62 could be made shorter to accommodate a smaller leg. Or, for example, the crosssectional shape of members 60, 62, and 64 may be modified so as to affect the degree of resiliency encountered at the position 225 of full extension.

Additional embodiments (not shown) may comprise adjustable attachments of high pivot point 66 or low pivot point 68 to upper orthotic assembly 10, so that the position and direction of application of various forces may be adjustable as needed to accomodate the particular patient.

Still further embodiments (not shown) may encompass changes in the position at which contact is made between surfaces 130, 132. For example, contact surface 130 may extend further posterior, in order to change the angle of leg extension at which contact is made between surfaces 130, 132, and which may furthermore change the amount of leg extension permitted to less than full extension in order to accommodate the needs of the particular patient.

Additional embodiments may be directed to modifications of the orthotic assemblies that attach the hinge to the leg, including alternative embodiments of upper orthotic assembly 10 and lower orthotic assembly 11. For example, upper orthotic assembly 10 comprises, generally, a means for maintaining two pivot points on the lateral side of the knee and, likewise, two pivot points on the medial side of the knee. Such a maintaining means can be accomplished by many different known types of assemblies, such as a combination of straps, or by other means.

Similarly, lower orthotic assembly 11 is not limited to the specific embodiment described, but generally includes all means for connecting the lower member 64 to the lower portion of the leg. For example, another embodiment (not shown) may comprise a pivotal connection between lower shell 40 and each lower member 64, with an anterior rigid member (not shown) connecting the two members 64 across the anterior of shell 40, so that each lower member 64 may rotate to a limited extent about shell 40, such rotation being limited by abutment of the anterior rigid member (not shown) against shell 40. In this alternative embodiment, it can be seen that the extension force in the direction of arrow 230 in FIG. 9 about single axis pivot 122 is translated directly to a posterior motion of single axis pivot point 122 while rotation of the lower arm is translated into a posterior force applied to the anterior of the tibia 203 in the direction of arrow 246 in FIG. 7, as a result of the contact between the lower shell 40 and the right member.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A knee orthosis for providing forces to restrain and restrict the movement of a leg during flexion and extension about the knee, comprising:
   an orthosis linkage having a central portion, a long upper member extending from said central portion, a short upper member extending from said central portion, and a lower member also extending from said central portion;
   means for pivotally connecting the long upper member to the upper portion of the leg, said pivotal connection being distal from the knee so that force applied to the long upper member is transmitted to a portion of the femur distal from the knee;
   means for pivotally connecting the short upper member to the upper portion of the leg, said pivotal connection being proximate to the knee so that force applied to the short upper member is transmitted to a portion of the femur proximate to the knee; and
   means for connecting the lower member to the lower portion of the leg.

2. The knee orthosis as recited in claim 1 wherein the knee orthosis further comprises means responsive to a portion of the extensional rotation of the leg for . translating said extensional rotation into a variably increasing force applied in an anterior direction to the lower portion of the leg, proximate to the knee.

3. The knee orthosis as recited in claim 2 wherein the translation means includes forces applied to the upper portion of the leg and to the lower portion of the leg, said forces being translated, simultaneously, from the orthosis linkage:
   through the long upper member to the upper portion of the leg;
   through the shorter upper member to the upper portion of the leg, at a location more proximate to the knee than the force applied by the long upper member; and
   through the lower member to the lower portion of the leg.

4. The knee orthosis as recited in claim 3 wherein said translating means are actuated at a first position within the range of 15° to 45° from full extension, and wherein said translating means are continually actuated between said first position and a second position of full extension.

5. The knee orthosis as recited in claim 4 wherein the force applied to the tibia by the translating means gradually increases as the leg rotates in extension from said first position to said second position.

6. The knee orthosis as recited in claim 3 wherein the translating means includes a first translation surface on the posterior side of the proximate end of the longer upper member, a second translation surface on the anterior side of the lower member proximate to the proximate end and means for slideably engaging the first and second translation surfaces so that force applied to the leg in extensional rotation is translated into a generally posterior force applied to the central portion of the orthosis linkage.

7. The knee orthosis as recited in claim 1 wherein the knee orthosis further comprises means responsive to a portion of the extensional rotation of the leg for shortening the overall length of the knee orthosis.

8. A knee orthosis for providing forces to restrain and restrict the movement of a leg during flexion and extension about the knee, comprising:
   an orthosis linkage having a central portion, and at least three members extending outwardly from the central portion, including a long upper member, a short upper member, and a lower member, each having a proximate end and a remote end with respect to the central portion;
   an upper orthotic assembly pivotally connected to the long upper member at a first remote pivot distal from the knee and pivotally connected to the short upper member at a second remote pivot proximate to the knee, the upper orthotic assembly also comprising means for affixing said assembly to the leg; and
   a lower orthotic assembly connected to the lower member, the lower orthotic assembly also comprising means for affixing said assembly to the leg.

9. The knee orthosis as recited in claim 8 wherein the orthosis linkage further comprises a first pivotal connection, connecting the long upper member to the shorter upper member, so that said first pivotal connection is rotatable about both the first and second remote pivots, said rotation of the first pivotal connection thereby defining a first arcuate path.

10. The knee orthosis as recited in claim 9 wherein the orthosis linkage further comprises a second pivotal connection, connecting the proximate end of the lower member to the short upper member, so that the second pivotal connection rotates about the second remote pivot, said rotation of the second pivotal connection thereby defining a second arcuate path.

11. The knee orthosis as recited in claim 10 wherein the first pivotal connection is positioned a first radial distance from the second remote pivot, and the second pivotal connection is positioned a second radial distance from the second remote pivot, and wherein the first radial distance is less than the second radial distance.

12. The knee orthosis as recited in claim 11 wherein the first pivotal connection and the second remote pivot define a first line, wherein the second pivotal connection and the second remote pivot define a second line, and wherein the angle between the first and second line is greater than zero.

13. The knee orthosis as recited in claim 12 wherein the second pivotal connection is positioned posterior to the first pivotal connection, throughout at least a portion of the second arcuate path.

14. The knee orthosis as recited in claim 12 wherein the second pivotal connection is positioned posterior to the first pivotal connection throughout the second arcuate path, so that as the first pivotal connection moves in a posterior direction, the second pivotal connection moves in a posterior and upward direction, thereby shortening the overall length of the knee orthosis.

15. The knee orthosis as recited in claim 13 wherein the orthosis linkage further comprises means for translating the rotation of the lower member about the second pivotal connection into a generally posterior force applied to the orthosis linkage.

16. The knee orthosis as recited in claim 15 wherein the long upper member on its proximate end has an extension piece extending beyond the first pivotal connection and wherein the translating means includes a first translation surface on the posterior side of the proximate piece, and further includes a second translation surface on the anterior side of the lower member proximate to the proximate end and means for slideably engaging the first and second translation surfaces so that force applied to the leg in extensional rotation is translated into a generally posterior force applied to the central portion of the orthosis linkage.

17. The knee orthosis as recited in claim 16 wherein the second translation surface on the lower member is distal of the second pivotal connection of the lower member so that an extensional rotation of the lower member within the contact arc is translated to a movement of the second pivotal connection within the second arcuate path.

18. The knee orthosis as recited in claim 8 wherein said upper orthotic assembly comprises an upper shell comprised of a hard resilient material suitable for installation of mechanical pivot points therein, the shape of said shell being conformed to approximate the shape of the leg above the knee.

19. The knee orthosis as recited in claim 18 wherein said upper orthotic assembly further comprises at least one strap to adjustably fasten said upper orthotic assembly to said upper portion of the leg, and further comprises an anterior plate affixed to said straps, said anterior plate conformed to a portion of the anterior of the leg.

20. The knee orthosis as recited in claim 8 wherein the lower orthotic assembly comprises a lower shell conformed to a portion of the lower portion of the leg, and further comprises a strap to substantially maintain the lower shell in position on the leg so that substantial longitudinal or rotational movement of said lower orthotic assembly about said leg is prevented.

21. The knee orthosis as recited in claim 20 wherein the lower shell comprises a hard resilient outer portion and a soft resilient inner portion.

22. The knee orthosis as recited in claim 8 wherein the proximate end of the short upper member comprises a first flat surface, the proximate end of the lower member comprises a second flat surface, and the proximate end of the long upper member comprises a third flat surface so that the first flat surface is slideable against both the second and third flat surfaces.

23. The knee orthosis as recited in claim 22 wherein the orthosis linkage comprises a cover plate attached to both the first and second pivotal connections of the side of the linkage opposite the short upper member, the cover plate comprising a fourth flat surface, wherein the proximate end of the lower member further comprises a fifth flat surface on the opposite side of the second flat surface, the proximate end of the long upper member further comprises a sixth flat surface on the opposite side of the third flat surface, both of said fifth and sixth flat surfaces being slidable with the fourth flat surface, whereby the proximate ends of the long upper member and the lower member are sandwiched between the fourth flat surface on the cover plate and the first flat surface on the short upper member.

24. The knee orthosis as recited in claim 8 wherein the knee orthosis comprises a second orthosis linkage similar to the first orthosis linkage, so that the first orthosis linkage may be positioned proximate to the medial side of the knee, and the second orthosis linkage may be positioned proximate to the lateral side of the knee.

25. The knee orthosis as recited in claim 16 wherein the first and second translation surfaces first make contact at a position corresponding to approximately 30° of full extension, said contact continuing throughout further extension.

26. The knee orthosis as recited in claim 16 wherein the first and second translation surfaces make contact at a position corresponding to a range of 15° to 45° of full extension, said contact continuing throughout further extension.

27. The knee orthosis as recited in claim 16 wherein the first and second translation surfaces make contact at a position corresponding to a range of 20° to 35° of full extension, said contact continuing throughout further extension.

28. A knee orthosis for providing forces to restrain and restrict the movement of a leg during flexion and extension about the knee, comprising:
an upper orthotic assembly including a hard resilient upper shell adapted to substantially conform to the shape of the adjacent portion of the leg, also including means for affixing said assembly to the leg;
a lower orthotic assembly including a hard resilient lower shell with a softer inner lining adapted to substantially conform to the shape of the adjacent portion of the leg, also including means for affixing the assembly to the leg; and,
two orthosis linkages, one of the medial side of the knee, the other on the lateral side of the knee, each having a central portion and at least three members having an end proximate to the central portion and an end remote from the central portion, including:
a lower member connected to the lower shell, and rotatably connected to the central portion at a single axis pivot,
a short upper member pivotally connected to the upper shell at its remote end, and
a long upper member pivotally connected to the upper shell at its remote end, and pivotally connected to the proximate end of the short upper member at its proximate end, said pivotal connection being affixed to the central portion at an upper pivot point, said long upper member having a portion extending from the upper pivot point, said extended portion having a slidable contact surface on its posterior edge and said lower member having a fulcrum surface on its anterior edge proximate to the central portion, so that the contact surface and the fulcrum surface slidably engage beginning at a first position within the range of 15° to 45° of full extension, and continually slidably engage between said first position and a second position of full extension.

29. A knee orthosis, comprising:
a first support member adopted to be secured to a leg on one side of the knee;
a second support member adapted to be secured to a leg on the side of the knee opposite that of said first support member;
a linkage connecting said support members comprising:
a first elongated, rigid arm having a proximate and a remote end with respect to the knee, said remote end of said first arm pivotally mounted on said first support member;
a second elongated, rigid arm having a proximate end and a remote end, said remote end of said second arm being pivotally mounted on said first support member at a location spaced apart from the location at which said first arm is pivotally mounted to said first support member,
said first and second arms being pivotally connected to one another at location adjacent their respective proximate ends; and
a third elongated, rigid arm having a remote end and a proximate end, said remote end of said third arm mounted on said second support member, said proximate end of said third arm being pivotally linked to said first support member through said first and second arms, whereby when said support members are attached to a leg on opposite sides of the knee some range of flexion and extension of the leg is permitted.

30. The knee orthosis as recited in claim 29 wherein the knee orthosis further comprises a central portion connecting the proximate ends of the first, second, and third arms, so that the first and second arms are pivotally connected on the central portion at a first pivotal connection, and the third arm is pivotally connected to the central portion at a second pivotal connection apart from the first pivotal connection.

31. The knee orthosis as recited in claim 30 wherein the proximate end of the first arm comprises a member extending from the first pivotal connection in a direction away from the remote end, said member having a slideable contact surface, and the third arm has a slideable fulcrum surface so that the contact surface and the fulcrum surface slideably engage during at least a portion of extension and flexion of the leg.

32. The knee orthosis as recited in claim 31 wherein the first arm is longer than the second arm.

33. The knee orthosis as recited in claim 31 wherein the contact surface and the fulcrum surface slideably engage beginning at a first position within the range of 15° to 45° of full extension, and continually slideably engage between said first position and a second position of full extension.

34. A method of providing forces to restrain and restrict the movement of a leg during flexion and extension about the knee, comprising the steps of:
first, providing a knee orthosis comprising an upper leg attachment, a lower leg attachment, and a linkage having an upper end and a lower end, said linkage connected to the upper leg attachment at its upper end, and connected to the lower leg attachment at its lower edge;
second, affixing the upper leg attachment to the upper portion of the leg, and affixing the lower leg attachment to the lower portion of the leg;
third, providing a first force in a posterior direction to the portion of the leg below, and proximate to the knee, said first force increasing in amount during extension so that at full extension said first force substantially impedes further extension;
fourth, providing a second force, in an anterior direction, to a portion of the leg above, and proximate to the knee, said second force being provided substantially simultaneously with the third step; and
fifth, providing a third force, in the posterior direction, to the portion of the leg above and remote from the knee and at a location substantially above that of the second force, said third force being provided substantial simultaneously with the third and fourth steps.

35. The knee orthosis as recited in claim 34, wherein the method includes a sixth step, where the knee orthosis becomes shorter in overall length during extension substantially simultaneously with the third, fourth and fifth steps.

36. The knee orthosis are recited in claim 34, wherein the first force is provided beginning within the range of 15° to 45° of full extension, and is provided substantially continuously to full extension.

37. The knee orthosis as recited in claim 34, wherein the first force is progressively increasing as the leg extends toward full extension.

* * * * *